May 27, 1958 M. COMBE Plant Pat. 1,712
ROSE PLANT
Filed Oct. 7, 1957
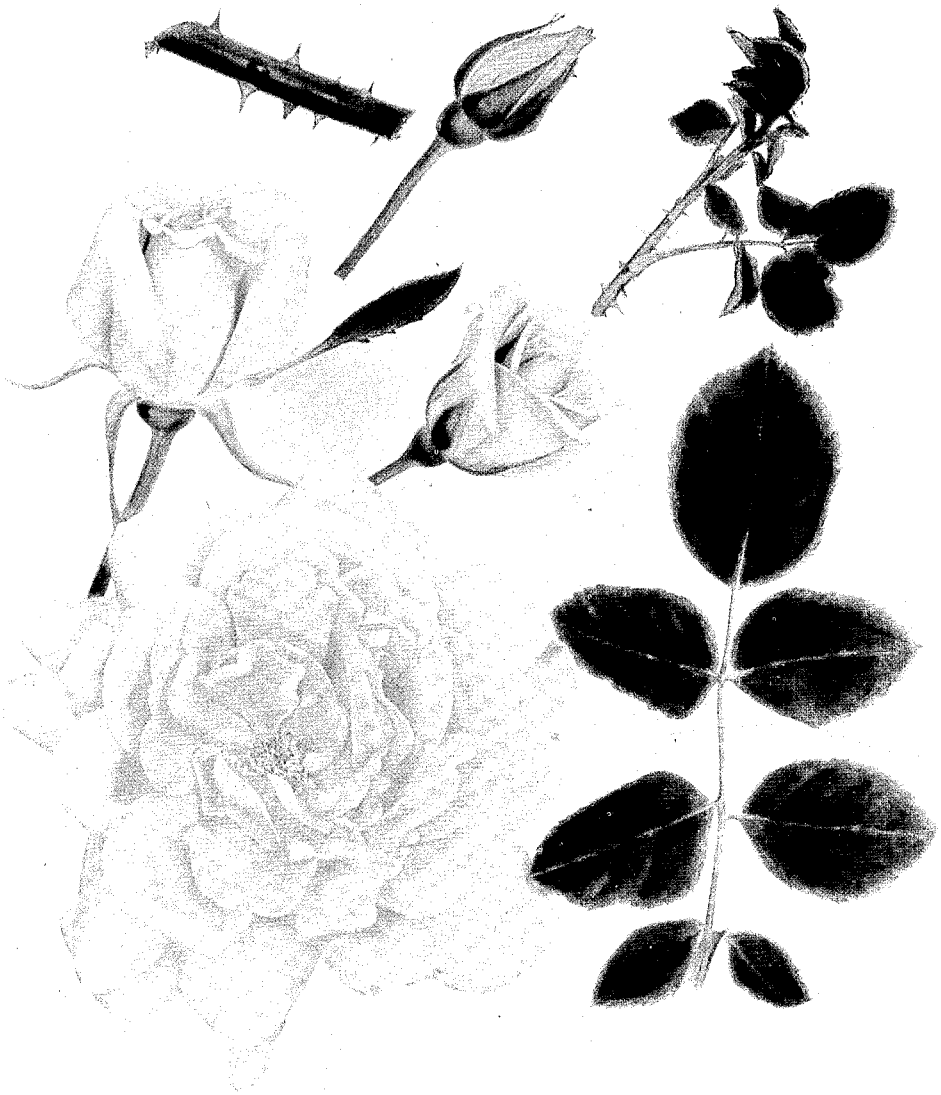
Inventor
Maurice Combe
By: Robb & Robb
Attorneys.

United States Patent Office

Plant Pat. 1,712
Patented May 27, 1958

1,712

ROSE PLANT

Maurice Combe, La Galochere par St. Martin d'Heres, France, assignor to Jackson & Perkins Company, Newark, N. Y., a corporation of New York Application October 7, 1957, Serial No. 688,796

1 Claim. (Cl. 47—61)

The present invention relates to a new and distinct variety of rose plant of the hybrid tea class, which was originated by me by crossing the variety "Peace" (Plant Patent No. 591) with an unnamed and unpatented seedling derived as a cross of "Peace"×"Orange Nassau" (Plant Patent No. 350).

The primary objective of this breeding was to obtain a new rose variety comparable to that of "Peace," but which bears more highly colored flowers. While the results achieved a highly colored hybrid tea rose of large size, the new variety did not otherwise correspond to the characteristics of "Peace," but nevertheless, achieved a new and distinct combination of characteristics which is desirable and attractive, as well as different from anything heretofore available, as evidenced by the following characteristics which are outstanding in the new variety:

(1) Young growth of distinctive Van Dyke Red general color tonality;

(2) Attractive buds;

(3) Flowers of large size;

(4) A distinctive Geranium Pink general color tonality of the flowers in which the centres of the petals are lightly overcast with Scarlet Red; and (5) Firmness and absence of fading of the flower color.

The foregoing characteristics and distinctions definitely differentiate the new variety from its parents, as well as from all other varieties of which I am aware, and asexual reproduction of the new variety by budding, as performed at Newark, New York, U. S. A., and also at Pleasanton, California, U. S. A., shows that these characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.

*Seed parent.*—"Peace."

*Pollen parent.*—An unnamed seedling derived as a cross of "Peace"×"Orange Nassau."

Classification:

*Botanic.*—Hybrid tea.

*Commercial.*—Hybrid tea.

*Flower*

(Observations made from specimens grown in a greenhouse at Newark, New York, U. S. A., in the early afternoon and during the latter part of the month of May.)

Blooming habit: Recurrent—continuous.

Bud:

*Size.*—Large.

*Form.*—Pointed; is not affected by wet or hot weather.

*Color.*—When sepals first divide—Scarlet, Plate 1. When petals begin to unfurl—Scarlet, Plate 1. When half-blown: inside of petals—Grenadine Pink, Plate 2, with edges of petals lightly overcast with Rose Doree, Plate 1; reverse of petals—Rose Doree, Plate 1, lightly overcast with Orange, Plate 3, in the lower half of the petal.

*Sepals.*—Slightly branched; curl back when petals begin to unfurl. Color: inside—Cerro Green, Plate 5; outside—Kildare Green, Plate 31.

*Calyx.*—Color—Spinach Green, Plate 5. Shape—apple. Size—large. Aspect—smooth. Odor when rubbed—none.

*Peduncle.* — Length — long. Aspect — rough. Strength—erect; heavy. Color—Oil Green, Plate 5.

*Opening.*—Opens up well; is not affected by adverse weather conditions.

Bloom:

*Size.*—Large. Average size when fully expanded—5 inches.

*Borne.*—Singly.

*Stems.*—Long; strong.

*Form (when first open).*—High-centered. Permanence—retains its form to the end.

*Petalage.*—Double (full but open center). Number of petals under normal conditions—from 45 to 50.

*Color.*—Center of flower—Scarlet, Plate 1. Outer petals—Geranium Pink, Plate 1, with outer edges of petals and upper half of petals lightly overcast with Capucine Buff, Plate 3. Base of petals (aiglet)—Light Cadmium, Plate 4. Inside of petals—Geranium Pink, Plate 1, with center of petals lightly overcast with Scarlet Red, Plate 1. Reverse of petals—Grenadine Pink, Plate 2, lightly overcast with Light Coral Red, Plate 13. General tonality from a distance—Geranium Pink, Plate 1, with center of petals lightly overcast with Scarlet Red, Plate 1.

*Discoloration.*—General tonality at end of first day—Geranium Pink, Plate 1, lightly overcast with Scarlet Red, Plate 1. Second day—Geranium Pink, Plate 1, lightly overcast with Grenadine Pink, Plate 2. Third day—Geranium Pink, Plate 1, lightly overcast with Grenadine Pink, Plate 2.

Petals:

*Texture.*—Thick; is not affected by wet or hot weather.

*Appearance.*—Inside—satiny. Outside—shiny.

*Form.*—Oval.

*Arrangement.*—Informal (with "rags" in center).

*Petaloids in center.*—Few; large.

*Persistence.*—Drop off cleanly.

*Fragrance.*—Moderate. Nature—tea (average hybrid tea scent).

*Lasting quality.*—On the plant—long. As cut flower—long.

*Genital organs*

Stamens, anthers: Medium size; many; regularly arranged around styles. Color—Cadmium Yellow, Plate 3.

Stamens, filaments (threads): Long. Color—Grenadine Pink, Plate 2.

Pollen: Color—Baryta Yellow, Plate 4.

Styles: Bunched; uneven length; medium length; thin.

Stigmas: Color—Spectrum Red, Plate 1.

Ovaries: All enclosed in calyx.

Hips: None.

Seeds: None.

*Plant*

Form: Bush.
Growth: Vigorous; upright; tall.
Foliage: Compound of 5 to 7 leaflets.
*Size.*—Large.
*Quantity.*—Abundant.
*Color.*—New foliage: upper side—Oil Green, Plate 5, with outer edges Oxblood Red, Plate 1; under side—Pomegranate Purple, Plate 12. Old foliage: upper side—Varley's Green, Plate 18; under side—Light Cress Green, Plate 31.
*Shape.*—Oval pointed.
*Texture.*—Upper side—leathery; glossy. Under side—smooth.
*Ribs and veins.*—Ordinary.
*Edge.*—Serrated (saw-toothed).
*Serration.*—Both double and single; small.
*Leaf stem.*—Color—Chrysolite Green, Plate 31. Under side—prickly.
*Stipules.*—Medium length; smooth.
Wood:
*New wood.*—Color—Van Dyke Red, Plate 13. Bark—smooth.

*Old wood.*—Color—Olive Green, Plate 4. Bark—smooth.
Thorns:
*Thorns.*—Quantity: on main stalks from base—many; on laterals from stalk—many. Form—flat base; medium length; hooked downward. Color (when young)—Carmine, Plate 1. Position—irregular.
*Prickles.*—Quantity: on main stalks—none; on laterals—none.
*Short needles.*—Quantity: on main stalks—none; on laterals—none.

I claim:

A new and distinct variety of rose plant of the hybrid tea class, substantially as herein shown and described, characterized particularly as to novelty by its dark colored Van Dyke Red young growth, the attractiveness of its buds, the large size of its flowers, the distinctive Geranium Pink general color tonality of its flowers, with their petal centers lightly overcast with Scarlet Red, and the firm retention of the flower color.

No references cited.